(12) United States Patent
Ondrla et al.

(10) Patent No.: US 6,228,119 B1
(45) Date of Patent: May 8, 2001

(54) MODULAR GLENOID ASSEMBLY

(75) Inventors: Jeffrey M. Ondrla, Lessburg; James A. Caywood, Warsaw, both of IN (US)

(73) Assignee: Depuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 09/321,778

(22) Filed: May 27, 1999

Related U.S. Application Data

(60) Provisional application No. 60/088,594, filed on Jun. 9, 1998, and provisional application No. 60/094,757, filed on Jul. 31, 1998.

(51) Int. Cl.$^7$ ................................................. A61F 2/40
(52) U.S. Cl. ................................................. 623/19.11
(58) Field of Search .......................... 623/19.11, 19.12, 623/19.13, 20.28, 20.21

(56) References Cited

U.S. PATENT DOCUMENTS

| | | | |
|---|---|---|---|
| 4,524,467 | * 6/1985 | DeCarlo, Jr. ................ | 603/22 |
| 4,795,468 | * 1/1989 | Hodorek et al. ............. | 623/18 |
| 4,964,865 | 10/1990 | Burkhead et al. . | |
| 4,986,833 | 1/1991 | Worland . | |
| 5,032,132 | * 7/1991 | Matsen, III et al. ......... | 623/19 |
| 5,080,673 | 1/1992 | Burkhead et al. . | |
| 5,593,448 | * 1/1997 | Dong ........................... | 623/19 |
| 5,702,447 | * 12/1997 | Walch et al. ................. | 623/16 |
| 5,800,551 | * 9/1998 | Williamson et al. ......... | 623/19 |

FOREIGN PATENT DOCUMENTS

| | | |
|---|---|---|
| 0 776 636 A1 | 6/1997 | (EP) . |
| 2 683 142 | 5/1993 | (FR) . |
| 2 695 313 | 3/1994 | (FR) . |
| 2 755 847 | 5/1998 | (FR) . |

OTHER PUBLICATIONS

"Biomet Biomodular Low Profile Modlar Glenoid," Biomet Corporation, one page, date unknown.
"Biomet Biangular Standard Metal Backed Glenoid," Biomet Corporation, one page, date unknown.
"Kirschner Integrated Shoulder System™ for Hemi and Total Shoulder Arthroplasty," Kirschner Medical Corporation, two pages, date unknown.
"The Cofield Total Shoulder System," Smith & Nephew Richards Inc., two pages, date unknown.
European Search Report, completed Sep. 10, 1999, mailed Sep. 17, 1999.

* cited by examiner

Primary Examiner—David H. Willse
Assistant Examiner—Alvin Stewart
(74) Attorney, Agent, or Firm—Maginot, Addison & Moore

(57) ABSTRACT

A modular glenoid assembly is provided for attachment to a glenoid surface of a scapula. The modular glenoid assembly includes a base adapted to couple with the glenoid surface and a bearing insert. The base includes a lip that defines a channel. The bearing insert includes a bearing surface adapted to engage a head portion of a humeral component and a tab. The tab is formed to be received within the channel and engage the lip when the insert is moved in a superior direction into position against the base.

19 Claims, 3 Drawing Sheets

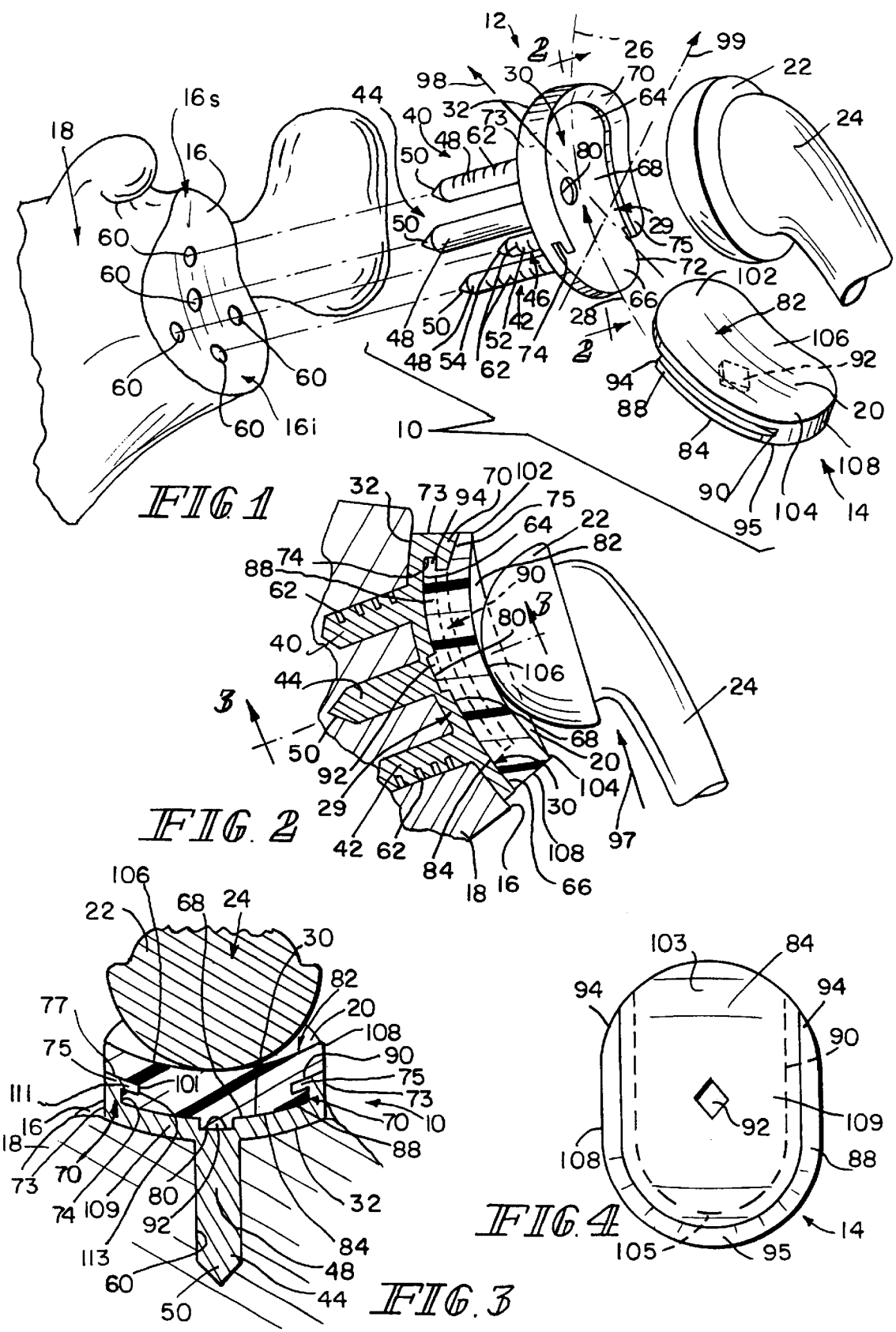

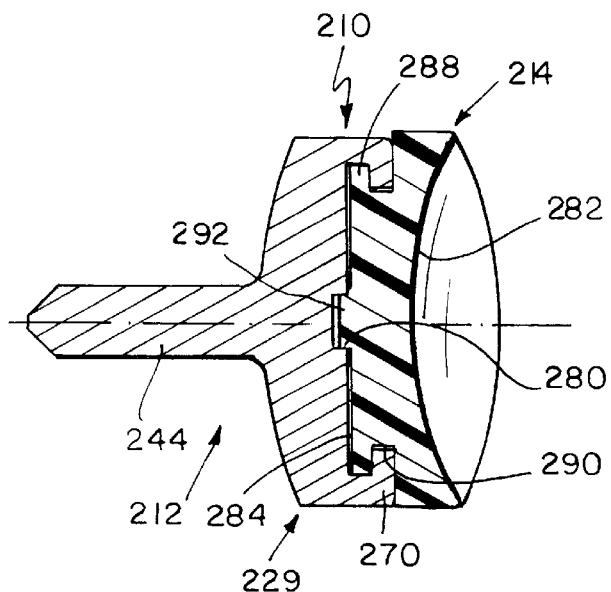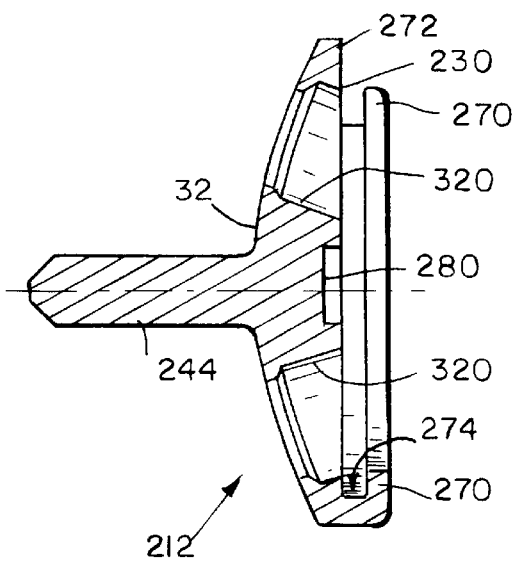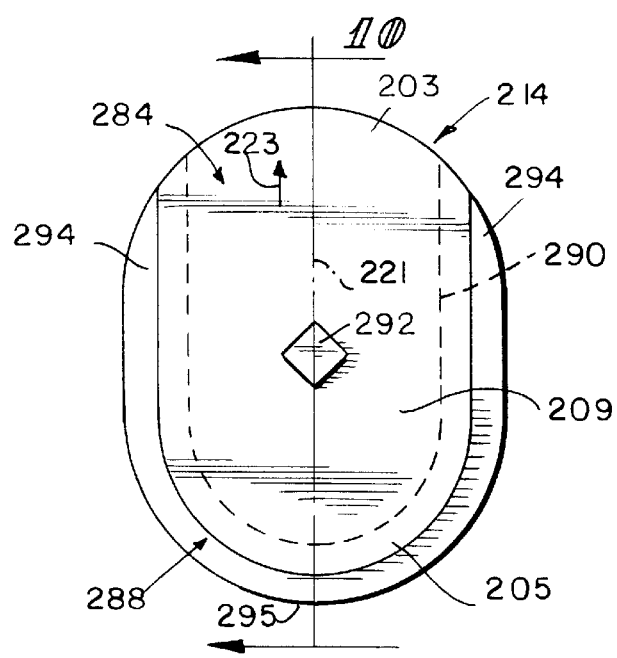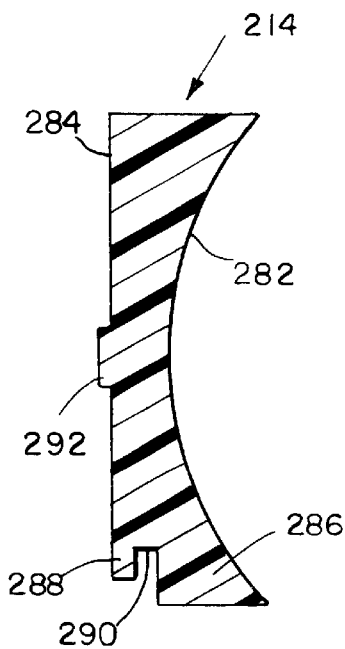

MODULAR GLENOID ASSEMBLY

This application claims priority under 35 U.S.C. §119(e) of Ser. No. 60/088,594 filed Jun. 9, 1998 in the United States Patent and Trademark Office and Ser. No. 60/094,757 filed Jul. 31, 1998 in the United States Patent and Trademark Office.

BACKGROUND AND SUMMARY OF THE INVENTION

The present invention relates to a prosthetic glenoid component and particularly to a modular glenoid assembly for attachment to a glenoid surface of a scapula to replace a natural socket of a shoulder and to provide a bearing surface for a head portion of an arm bone or humerus. More particularly, the present invention relates to a modular glenoid assembly comprising a metal backed base coupled to a plastic bearing insert.

According to the present invention a modular glenoid assembly is provided that comprises a base adapted to couple with the glenoid surface and a bearing insert providing a bearing surface adapted to engage the head portion of the humerus. The base is provided with a first connector portion and the insert is provided with a second connector portion. In addition, the first and second connector portions are engageable and proportional to secure the insert to the base when the insert is moved into engagement with the base.

In preferred embodiments, the first connector portion includes a channel extending about a portion of the base and the second connector portion includes a tab extending about a portion of the insert. The tab is received in engagement with the channel when the insert is moved in a superior direction into position against the base. In addition, the channel includes inferiorly and inwardly opening portions and the tab includes superiorly and outwardly extending portions to be received respectively in the inferiorly and inwardly extending portions.

Further, according to the present invention a modular glenoid assembly for attachment to a glenoid surface of a scapula to provide a bearing surface is provided that comprises a base adapted to couple with the glenoid surface and a bearing insert. The base includes a lip and the bearing insert includes a bearing surface adapted to engage the head portion of the humeral component and a tab formed to engage the lip when the insert is moved in a superior direction into position against the base.

Still further in accordance with the present invention a modular glenoid assembly is provided that comprises a metal base and a plastic bearing insert. The metal base includes a lower surface, an upper surface, at least one peg extending from the lower surface, and a lip extending about a portion of the upper surface and defining a channel. The bearing insert includes bearing surface, an opposite lower surface facing the upper surface of the base, and a tab extending about a portion of the lower surface. The tab is received in the channel from an inferior to a superior direction to mount the insert on the base.

Additional features of the present invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 1 is an exploded perspective view of a modular glenoid assembly in accordance with the present invention positioned between a glenoid surface of a scapula and a humeral component showing the glenoid assembly including a base having upper and lower surfaces, pegs extending from the lower surface, a recessed portion formed in the upper surface, and a lip extending about a portion of the upper surface a bearing insert formed to include a bearing surface and a lower surface including a tab engagable and proportional to the lip;

FIG. 2 is an assembled sectional view taken along lines 2—2 of FIG. 1 showing the pegs of the base received within apertures formed in the glenoid surface and the bearing insert mounted on the base positioning the bearing surface in engagement with the humeral component;

FIG. 3 is a sectional view taken along lines 3—3 of FIG. 2 showing the lip of the base including a channel and the tab of the insert received in the channel;

FIG. 4 is a bottom view of the bearing insert of FIG. 3 showing the lower surface of the insert including an inferior end, a superior end, and a central portion, the detent extending from the central portion and the tab extending about the superior end and central portion of the insert;

FIG. 7 is a sectional view of an alternative embodiment of a glenoid assembly in accordance with the present invention showing a base including a generally flat upper surface, a lower surface, a peg extending from the lower surface, and an outer lip extending about a portion of the upper surface and a bearing insert including a generally flat lower surface configured for mating with the upper surface of the base;

FIG. 8 is a sectional view of the base of FIG. 7 showing screw holes extending through the base between the upper and lower surfaces and the peg positioned to lie between the spaced-apart screw holes;

FIG. 9 is a bottom view of the bearing insert of FIG. 7 showing the lower surface of the insert including an inferior end, a superior end, and a central portion and the tab extending about the superior and central portion of the insert; and FIG. 10 is a view taken along lines 10—10 of FIG. 9 showing the bearing insert having a generally flat lower surface.

DETAILED DESCRIPTION OF THE DRAWINGS

Figure 5:
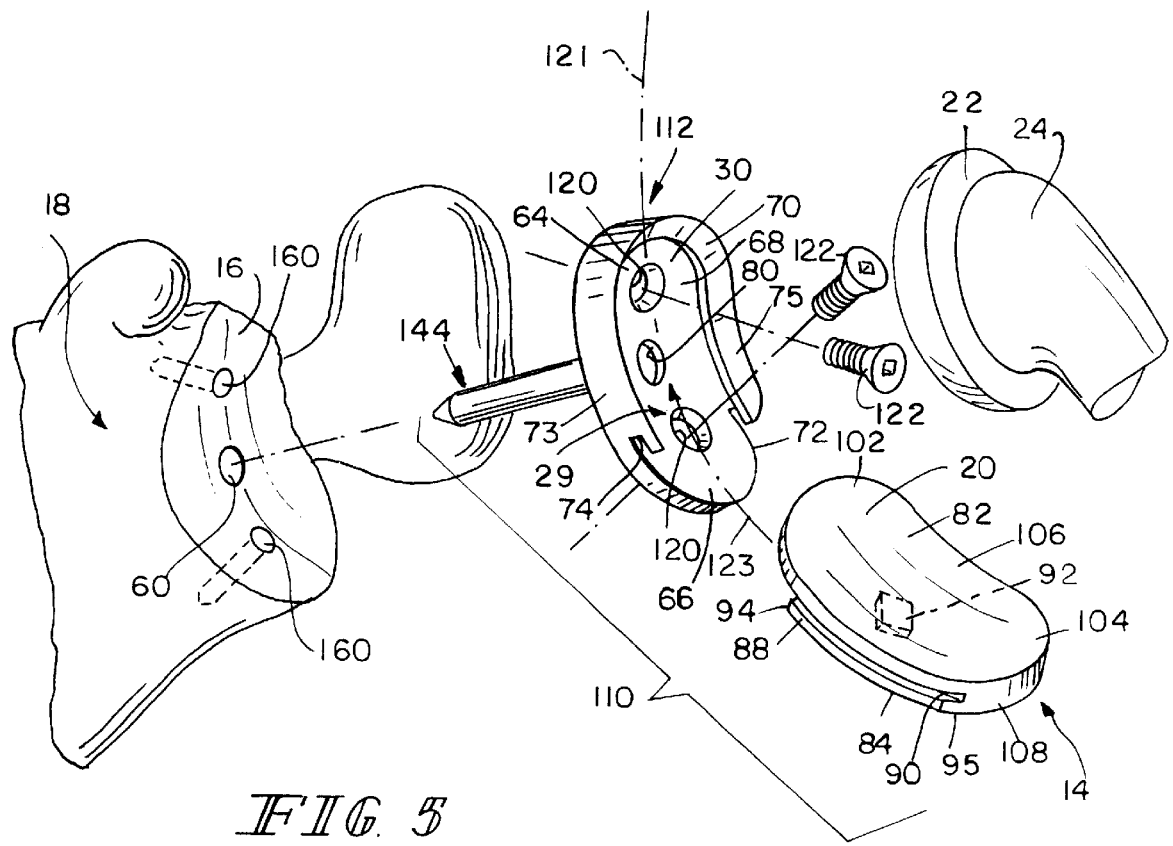
FIG. 5 is a view similar to FIG. 1 of an alternative embodiment of a base that is suitable for use with the insert showing the base having upper and lower surfaces, two apertures extending between the upper and lower surfaces for receiving screws in order to couple the base to the scapula, a peg extending from the lower surface of the base, a lip extending about a portion of the upper surface, and a recessed portion formed in the upper surface for receiving the detent of the insert.

A modular glenoid assembly 10 is provided in accordance with the present invention. FIG. 1 shows glenoid assembly 10 located between a glenoid surface 16 of a scapula 18 and a head portion 22 of a humeral component 24. The glenoid surface 16 has an inferior portion 16i and a superior portion 16s as shown in FIG. 1. Glenoid assembly 10 is designed to be attached to glenoid surface 16 of scapula 18 to replace the natural glenoid surface. Glenoid assembly 10 includes a base 12 provided with a first connector portion and a bearing insert 14 provided with a second connector portion that is slidably received by first connector portion of base 12 along an axis 26 in a superior direction 28. First and second connector portions are engageable and proportional to secure the insert 14 to base 12 when insert 14 is moved into engagement with base 12. Thus, glenoid assembly 10 resists physiologic loading by rotator cuff and deltoid muscles (not shown).

Base 12 of modular glenoid assembly 10 is formed to include a body 29 that has a concave upper surface 30 positioned to face insert 14 and a convex lower surface 32 positioned to face glenoid surface 16. See FIG. 1. Superior, inferior, and center attachment pegs 40, 42, 44, respectively, are formed to extend from lower surface 32 to anchor body 29 to glenoid surface 16. A right stabilizing peg 46 and a similarly formed left stabilizing peg (not shown) additionally extend from lower surface 32.

Attachment pegs 40, 42, 44 each include a generally cylindrical body portion 48 and a generally conical tip portion 50, as shown in FIG. 1. Stabilizing pegs 46 also include a generally cylindrical body portion 52 and a generally conical tip portion 54. Glenoid surface 16 is formed to include apertures 60 aligned for receiving respective attachment pegs 40, 42, 44 and stabilizing pegs 46. Tip portions 50, 54 facilitate insertion of the pegs 40, 42, 44, 46 into apertures 60 of glenoid surface 16. The diameter of body portions 48, 52 is slightly less than the diameter of apertures 60 in order to provide space for a cement mantle (not shown) around the inner circumference of apertures 60 or to allow for interference fit. It is understood that pegs 40, 42, 44, 46 may be a wide variety of shapes and sizes in accordance with the present invention.

As shown in FIG. 2, superior and inferior pegs 40, 42 are each formed to include a plurality of notches or serrations 62. Serrations 62 increase the area of contact between pegs 40, 42 and the cement mantle (not shown) placed within apertures 60 to strengthen the bond between pegs 40, 42 and the bone of glenoid surface 16. Referring again to FIG. 1, each stabilizing peg 46 is also formed to include notches or serrations 62 so that the bone cement may secure stabilizing pegs 46 to the bone of the glenoid surface 16. It is within the scope of the present invention to form serrations 62 on one or more pegs 40, 42, 44, 46. It is also within the scope of the present invention to include pegs 40, 42, 44, 46 having a porous coating also for strengthening the bond between the pegs and the bone of glenoid surface 16. A more detailed description of pegs 40, 42, 44, 46 may be found in U.S. Pat. No. 5,032,132, entitled "Glenoid Component", to Frederick A. Matsen, III, which is incorporated herein by reference. While pegs 40, 42, 44, 46 are illustrated and described, it is within the scope of this disclosure to use a wide variety of attachment mechanisms to couple base 12 and scapula 18 together.

Referring now to FIG. 1, upper surface 30 of body 29 is formed for sliding engagement with bearing insert 14. Upper surface 30 includes a superior end 64, an inferior end 66, a center portion 68 positioned to lie between superior and inferior ends 64, 66, and a perimeteral edge 72. In addition, a first connector portion or outer lip 70 extends from perimeteral edge 72 adjacent to superior end 64 and center portion 68. As shown in FIGS. 2 and 3, outer lip 70 includes a side wall 73 extending from upper surface 30 and a tab 75 extending from side wall 73 over upper surface 30 to define a channel 74. Tab 75 includes a tapered surface 77 that faces insert 14 (See FIG. 3). Channel 74 is defined by upper surface 30 and lip 70 and includes inferiorly and inwardly opening portions. Channel 74 is generally U-shaped and extends, as stated above, only partially about perimeter edge 72 so that inferior end 66 of base 12 is spaced apart from lip 70.

As shown in FIG. 2, center portion 68 of upper surface 30 is also formed to include a recessed portion 80. Recessed portion 80 cooperates with bearing insert 14 to provide the surgeon with the feel of snap-fit. Recessed portion 80 is generally oval in shape, although it is within the scope of this disclosure to form recessed portion in a wide variety of shapes and patterns within upper surface 30. It is within the scope of this disclosure to form upper surface 30 without recessed portion, with greater than one recessed portion, or with a detent (not shown) thereon to cooperate with a recessed portion in insert. Base 12 is constructed from metal such as titanium alloy, however, it is within the scope of this disclosure to form base from a wide variety of metals such as cobalt chrome alloy and stainless steel. In addition, base 12 is preferably highly polished.

Bearing insert 14 is formed for sliding engagement with base 12 and provides a bearing surface 20 for head portion 22. As shown in FIG. 1, insert 14 includes a concave upper surface 82 facing head portion 22 and an opposite convex lower surface 84. Upper surface 82 of insert 14 provides bearing surface 20 for head portion 22 of humeral component 24 as shown in FIGS. 2, 4, and 5. Upper surface 82 includes a superior end 102, an inferior end 104, and a central portion 106 positioned to lie between superior and inferior ends 102, 104. An insert-perimeter edge 108 extends between upper and lower surfaces 82, 84. Edge 108 is formed to include a groove 90 therein. Groove 90 extends into perimeter edge 108 adjacent to superior end 102 and central portion 106 and is sized to receive tab 75 of lip 70 therein. As shown in FIG. 3, groove 90 is defined by a bottom surface 101, a top surface 111 and a side wall 113. Groove 90 is generally U-shaped and extends, as stated above, only partially about edge 108 so that inferior end 104 is spaced apart from groove 90. When assembled, groove 90 and channel 74 are situated in a general stacked alignment with one another.

As shown in FIG. 3, when assembled, lower surface 84 of insert 14 rests upon upper surface 30 of base 12. Lower surface 84 includes a superior end 105, an inferior end 103, and a central portion 109 positioned to lie between superior and inferior ends 105, 103. See FIG. 4. Lower surface 84 is also formed to include a second connector portion or tab 88 that extends into channel 74 and engages lip 70 and upper surface 30. Tab 88 extends adjacent to groove 90 about superior end 105 and central portion 109 of lower surface 84. Tab 88 has a top end 94 and a bottom end 95 at inferior end 103 of lower surface 84. Thus, tab 88 includes superiorly and outwardly extending portions that are received respectively in the inferiorly and inwardly extending portions of channel 74.

Once base 12 and insert 14 are assembled, lower surface 84 of insert 14 rests upon upper surface 30 of base 12. Insert 14 also includes a detent 92 extending from central portion 109 of lower surface 84. Detent 92 cooperates with recessed portion 80 to provide the feel of a snap-fit assembly. Detent 92 is rectangular in shape, although it is within the scope of this disclosure to form detent 92 in any number of shapes or sizes having greater or fewer than one detent, or form lower surface 84 to include a recess to interact with a corresponding detent (not shown) on base 12. Insert 14 is constructed of ultra high molecular weight polyethylene (UHMWPE), however, it is within the scope of the invention to manufacture insert 14 from a wide variety of materials suitable for orthopaedic use.

In assembling glenoid assembly 10, insert 14 is moved upward or in superior direction 28 along axis 26, as shown in FIG. 1. Tab 88 first engages inferior end 66 of upper surface 30. As insert 14 slides in direction 28 relative to base 12 along axis 26, tab 88 is received within channel 74 of base 12, as shown in FIGS. 2 and 3. Additionally, tab 88 of lower surface 84 is received within channel 74 and tab 75 of outer lip 70 of base 12 is received within groove 90 of insert 14.

Tab 88 of lower surface 84 moves in direction 28 within channel 74 until top end 94 of tab 88 engages side wall 73 of lip 70 adjacent to superior end 64. Detent 92 is formed to be received by recessed portion 80 of base 12 so that during assembly, detent 92 "snaps" into engagement with recessed portion 80 notifying the surgeon that insert 14 is mounted on base 12. Side wall 73 of outer hip 70 at superior end 64 also acts as a stop for top end 94 of tab 88. Once insert 14 is mounted on base 12, as shown in FIGS. 2 and 3, bearing surface 20 is ready to engage head portion 22 of humeral component 24. It is also within the scope of the present disclosure to include a ramp (not shown) on upper surface 30 for detent 92 to slide upon in order to more easily guide detent 92 into recessed portion 80.

Once implanted within glenoid surface 16 of scapula 18, glenoid assembly 10 encounters loading forces from rotator cuff muscles (not shown) and the deltoid muscle (not shown). As shown in FIG. 2, these loading forces are generally oriented in a superior direction 97. Glenoid assembly 10 may also encounter forces in an anterior/superior direction 98 or a posterior/superior direction 99, as shown in FIG. 1. Because of the generally superior direction 97 of the loading on glenoid assembly 10, insert 14 is prevented from disengaging base 12.

Figure 6:
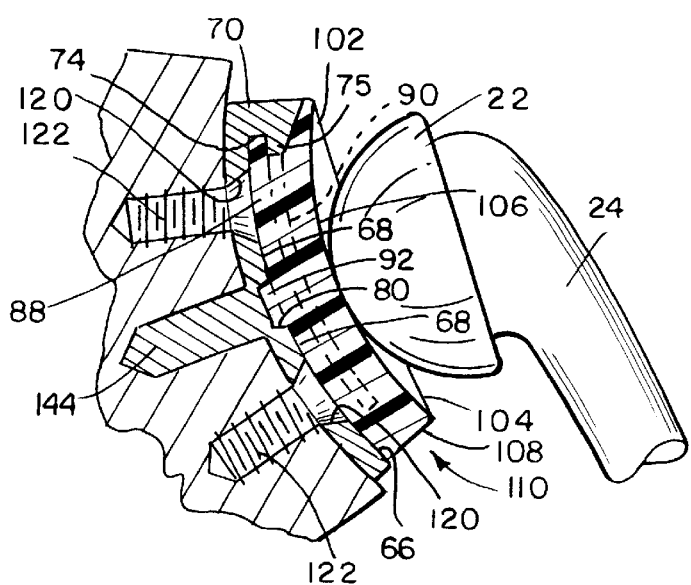
FIG. 6 is a view similar to FIG. 2 of the base and insert of FIG. 5 showing the peg and the screws received in the scapula and the lip of the base including a channel that receives the tab to couple the bearing insert to the base.

An alternative embodiment of glenoid assembly 110 in accordance with the present invention is shown in FIGS. 5 and 6. Assembly 110 includes a base 112 that slidingly receives bearing insert 14 along an axis 121 in a superior direction 123. Base 112 is formed similarly to base 12 and like reference numerals will be used to denote like components. Base 112 includes an attachment peg 144 that extends from lower surface 32 adjacent to center portion 68. Peg 144 is formed in a manner similar to pegs 40, 42, 44. It is appreciated, however, that peg 144 may be formed in a variety of shapes and sizes in accordance with the present invention. Peg 144 is received by pre-formed aperture 60 in glenoid surface 16. As shown in FIG. 5, body 29 includes two holes 120 therethrough that are sized to receive corresponding screws 122. As shown in FIG. 6, when fully assembled, screws 122 extend through holes 120 and into pre-formed apertures 160 in glenoid surface 16. Thus, screws 122 cooperate with peg 144 to couple base 112 to glenoid surface 16 of scapula 18. Base 112 is constructed of materials similar to base 12.

The assembly method of glenoid assembly 110 is similar to that described above in reference to glenoid assembly 10. Insert 14 slides along superior/inferior axis 121 in direction 123 so that tab 88 of lower surface 84 is received within channel 74 of base 112. At this time, tab 75 of lip 70 is received within groove 90 of insert 14. It becomes evident to the surgeon that insert 14 received within base 112 when detent 92 and recessed portion 80 produce a snap-in feel.

An additional embodiment of the present invention is shown in FIGS. 7–10. As shown in FIG. 7, glenoid assembly 210 is provided that includes a base 212 and a bearing insert 214. Base 212 of glenoid assembly 210 is coupled to glenoid surface 16 in a manner similar to base 112. Base 212 includes a body 229 that has a lower surface 232 configured for engagement with glenoid surface 16 and a generally planar upper surface 230. Upper surface 230 includes a superior end 264, an inferior end 266, and a center portion 268 positioned to lie between superior and inferior ends 264, 266. An outer lip 270 extends from upper surface 230 about superior end 264 and center portion 268. Lip 270 is formed in a manner similar to lip 70 of base 12, as previously described and includes a channel 274 therein. Channel 274 is generally U-shaped and formed in a manner similar to channel 74. In addition, as shown in FIG. 7, upper surface 230 of base 212 is formed to include a recessed portion 280 therein. Recessed portion 280 is similar to recessed portion 80 and cooperates with insert 214 to provide the snap-in feel previously described.

Referring now to FIG. 8, body 229 includes spaced apart screw holes 320 therethrough. Screw holes 320 extend between lower and upper surfaces 232, 230 and are spaced apart about an attachment peg 244. Screw holes 320 are sized for extension of screws (not shown) therethrough. It is within the scope of the present disclosure that base 212 be formed with greater or fewer than two screw holes 320. Peg 244 extends from lower surface 232 of base 212 and is formed to be received within pre-formed apertures 60 (see FIG. 5) within glenoid surface 16. Screws (not shown) extend through holes 320 of base 212 and into apertures 160 (see FIG. 5) formed in glenoid surface 16.

Turning now to FIGS. 9 and 10, bearing insert 214 cooperates with head 22 in a manner similar to insert 14 as previously described. Insert 214 includes a generally planar lower surface 284 and an opposite concave upper surface 282. Upper surface 282 is formed in a manner similar to upper surface 82 as previously described. Lower surface 284 includes a superior end 203, an inferior end 205, and a center portion 209 positioned to lie between superior and inferior ends 203, 205. A tab 288 is formed in lower surface 284. As shown in FIG. 9, tab 288 includes a top end 294 and a bottom end 295.

The assembly method of glenoid assembly 210 is similar to that described above in reference to glenoid assemblies 10, 110. Insert 214 slides along superior/inferior axis 221 in direction 223 so that tab 288 is received within channel 274 of base 112. At this time, lip 270 is received within groove 290 of insert 214. It becomes evident to the surgeon that insert 214 is received within base 212 when detent 292 and recessed portion 280 of base 212 produce a snap-in feel.

To couple assemblies 10, 110, 210 to scapula 18 the surgeon performs the following steps. Scapula 18 is sized and reamed in accordance with well known surgical procedures. At least one hole 60 is drilled within glenoid surface 16 to correspond with peg(s) on base 12, 112, 212 respectively. Base 12, 112, 214 is implanted within scapula 18 with channel 70, 270 opened inferiorly. Insert 14, 14, 214 is then slid into respective base 12, 112, 212 from inferior to superior direction. Thus, locking mechanism of the present invention utilizes a tongue-in-groove or tab-in-slot design. The metal base 12, 112, 214 is oriented such that the insert 14, 14, 214 slides in from an inferior to superior direction once the metal base 12, 112, 212 is securely fixed to glenoid 18.

Although the invention has been described in detail with reference to a preferred embodiment, variations and modifications exist within the scope and spirit of the invention as described and defined in the following claims.

What is claimed is:

1. A modular glenoid assembly for attachment to a glenoid surface of a scapula to provide a bearing surface, the modular glenoid assembly comprising:

a base having (i) a lower surface adapted to couple with the glenoid surface, (ii) an upper surface, (iii) a superior end, (iv) an inferior end, (v) a center portion, (vi) a perimeteral edge, and (vii) a lip which defines a channel, wherein the lip extends around a portion of the perimeteral edge at the superior end; and a bearing insert including (i) a bearing surface adapted to slidably engage a head portion of a humeral component, and (ii) a tab formed to be engaged within the channel of the lip when the insert is moved into position against the base, wherein both the lip and the channel are generally U-shaped.

2. A modular glenoid assembly comprising:

a metal base including a lower surface, an upper surface, an inferior end, a superior end, a center portion, a perimeteral edge, at least one peg extending from the lower surface, and a lip extending about a portion of the perimeteral edge at the superior end and defining a channel; and a plastic bearing insert including a bearing surface adapted to slidably engage a head portion of a humeral component, an opposite lower surface facing the upper surface of the base, and a tab extending about a portion of the lower surface, the tab being received in the channel from a first direction to a second direction to mount the insert on the base, wherein both the lip and the channel are generally U-shaped.

3. A method of coupling a glenoid assembly to a glenoid surface of a scapula, the glenoid surface having a superior portion and an inferior portion, comprising the steps of:

providing a base of the glenold assembly, the base including a first connector portion;

coupling the base to the glenoid surface;

providing an insert of the glenoid assembly, the insert being configured to contact a head portion of a humeral component, and further the insert having a second connector portion; and engaging the first connector portion with the second connector portion so as to couple the insert to the base, wherein (i) movement from the inferior portion to the superior portion of the glenoid surface defines a superior direction, and (ii) the insert is moved from the inferior portion toward the superior portion in relation to the base in the superior direction during the engaging step.

4. The method of claim 3, further comprising the step of providing loading forces to the glenoid assembly in the superior direction with a muscle after the insert is coupled to the base.

5. The method of claim 4, wherein the muscle is a deltoid muscle or a rotator cuff muscle.

6. The method of claim 3, wherein:

the first connector portion includes a channel extending about a portion of the base, the second connector portion includes a tab extending about a portion of the insert, and the engaging step includes the step of receiving the tab within the channel when the insert is moved in relation to the base in the superior direction.

7. The method of claim 3, wherein:

the base includes a generally concave upper surface, the insert includes a generally convex lower surface, and the generally concave upper surface contacts the generally convex lower surface during the engaging step.

8. The method of claim 3, wherein:

the base includes a generally flat upper surface, the insert includes a generally flat lower surface, and the generally flat upper surface contacts the generally flat lower surface during the engaging step.

9. A method of coupling a glenoid assembly to a glenoid surface of a scapula, the glenoid surface having a superior portion and an inferior portion, comprising the steps of:

providing a base of the glenoid assembly, the base including a lip;

coupling the base to the glenoid surface;

providing an insert of the glenoid assembly, the insert being configured to contact a head portion of a humeral component, and further the insert having a tab; and engaging the tab within the lip so as to couple the insert to the base, wherein (i) movement from the inferior portion to the superior portion of the glenoid surface defines a superior direction, and (ii) the insert is moved from the inferior portion toward the superior portion in relation to the base in the superior direction during the engaging step.

10. The method of claim 9, wherein:

the lip defines a channel which extends about a portion of the base, and the engaging step includes the step of receiving the tab within the channel when the insert is moved in relation to the base in the superior direction.

11. The method of claim 9, further comprising the step of providing loading forces to the glenoid assembly in the superior direction with a muscle after the insert is coupled to the base.

12. The method of claim 11, wherein the muscle is a deltoid muscle or a rotator cuff muscle.

13. The method of claim 9, wherein:

the base includes a generally concave upper surface, the insert includes a generally convex lower surface, and the generally concave upper surface contacts the generally convex lower surface during the engaging step.

14. The method of claim 9, wherein:

the base includes a generally flat upper surface, the insert includes a generally flat lower surface, and the generally flat upper surface contacts the generally flat lower surface during the engaging step.

15. A method of coupling a glenoid assembly to a glenoid surface of a scapula, the glenoid surface having a superior portion and an inferior portion, comprising the steps of:

providing a metal base of the glenoid assembly, the metal base including a lip extending about a portion of an upper surface of the metal base and defining a channel;

coupling the metal base to the glenoid surface;

providing an insert of the glenoid assembly, the insert being configured to contact a head portion of a humeral component, and further the insert having a tab extending about a portion of a lower surface of the insert; and engaging the tab within the channel so as to couple the insert to the base, wherein (i) movement from the inferior portion to the superior portion of the glenoid surface defines a superior direction, and (ii) the insert is moved in the superior direction during the engaging step from the inferior portion toward the superior portion of the glenoid surface.

16. The method of claim 15, further comprising the step of providing loading forces to the glenoid assembly in the superior direction with a muscle after the insert is coupled to the base.

17. The method of claim 16, wherein the muscle is a deltoid muscle or a rotator cuff muscle.

18. The method of claim 15, wherein:

the base includes a generally concave upper surface, the insert includes a generally convex lower surface, and the generally concave upper surface contacts the generally convex lower surface during the engaging step.

19. The method of claim 15, wherein:

the base includes a generally flat upper surface, the insert includes a generally flat lower surface, and the generally flat upper surface contacts the generally flat lower surface during the engaging step.

\* \* \* \* \*